(12) United States Patent
Divan et al.

(10) Patent No.: US 10,793,964 B2
(45) Date of Patent: Oct. 6, 2020

(54) PRE-TREATED FUNCTIONALIZED MULTI-WALLED CARBON NANOTUBE BASED METHANE SENSOR

(71) Applicant: UChicago Argonne, LLC, Chicago, IL (US)

(72) Inventors: Ralu Divan, Darien, IL (US); M. Tanim Humayun, Chicago, IL (US); Igor Paprotny, Chicago, IL (US); Lara A. Gundel, Berkeley, CA (US)

(73) Assignees: UChicago Argonne, LLC, Chicago, IL (US); The Regents of the University of California, Oakland, CA (US)

(*) Notice: Subject to any disclaimer, the term of this patent is extended or adjusted under 35 U.S.C. 154(b) by 253 days.

(21) Appl. No.: 15/146,718

(22) Filed: May 4, 2016

(65) Prior Publication Data
US 2017/0322174 A1 Nov. 9, 2017

(51) Int. Cl.
| | | |
|---|---|---|
| *C25D 9/08* | (2006.01) | |
| *G01N 33/00* | (2006.01) | |
| *G01N 27/30* | (2006.01) | |
| *G01N 27/12* | (2006.01) | |
| *C01B 32/168* | (2017.01) | |

(52) U.S. Cl.
CPC .............. *C25D 9/08* (2013.01); *C01B 32/168* (2017.08); *G01N 27/127* (2013.01); *G01N 27/308* (2013.01); *G01N 33/0047* (2013.01); *C01B 2202/06* (2013.01)

(58) Field of Classification Search
None
See application file for complete search history.

(56) References Cited

U.S. PATENT DOCUMENTS

| | | | |
|---|---|---|---|
| 6,919,730 B2 | 7/2005 | Cole et al. | |
| 6,949,931 B2 | 9/2005 | Cole et al. | |
| 7,074,310 B2 | 7/2006 | Smalley et al. | |
| 7,122,165 B2* | 10/2006 | Wong ................... | B82Y 30/00 |
| | | | 423/447.2 |
| 7,426,067 B1 | 9/2008 | Bright et al. | |
| 7,452,452 B2 | 11/2008 | Ren et al. | |
| 8,087,151 B2 | 1/2012 | Park et al. | |

(Continued)

FOREIGN PATENT DOCUMENTS

| | | |
|---|---|---|
| EP | 2 044 424 | 4/2009 |
| WO | WO-2007/089550 | 8/2007 |

(Continued)

OTHER PUBLICATIONS

Li, et al., Atomic Layer Deposition of ZnO on Multi-walled Carbon Nanotubes and Its Use for Synthesis of CNT—ZNO Heterostructures, Nano Express Col. 5, Aug. 7, 2010, pp. 1836-1840 (Year: 2010).*

(Continued)

*Primary Examiner* — Matthew D Krcha
(74) *Attorney, Agent, or Firm* — Foley & Lardner LLP

(57) ABSTRACT

A method of manufacturing a functionalized pre-treated carbon nanotube. Atomic Layer deposition is utilized to functionalize a pre-treated carbon nanotube. The functionalized pre-treated carbon nanotube may be used in a chemiresistor, including for methane detection.

9 Claims, 14 Drawing Sheets

(56) References Cited

U.S. PATENT DOCUMENTS

| | | | |
|---|---|---|---|
| 2009/0038681 A1* | 2/2009 | Trancik | H01G 9/2022 |
| | | | 136/256 |
| 2010/0089772 A1* | 4/2010 | Deshusses | G01N 27/127 |
| | | | 205/781 |
| 2011/0206932 A1 | 8/2011 | Waki et al. | |
| 2012/0042713 A1 | 2/2012 | Kim et al. | |
| 2013/0221346 A1 | 8/2013 | Lu et al. | |
| 2013/0224377 A1* | 8/2013 | Jensen | B01J 20/286 |
| | | | 427/237 |
| 2014/0311221 A1* | 10/2014 | Gole | G01N 27/127 |
| | | | 73/31.06 |
| 2015/0008486 A1 | 1/2015 | Bryant et al. | |

FOREIGN PATENT DOCUMENTS

| | | | |
|---|---|---|---|
| WO | WO-2008/010638 | 1/2008 | |
| WO | WO-2011/043620 | 4/2011 | |
| WO | WO-2015167637 A2 * | 11/2015 | B82Y 30/00 |

OTHER PUBLICATIONS

Qu, et al., Polymer-masking for controlled functionalization of carbon nanotubes, Chem Commun., 2007, 3859-3861. (Year: 2007).*

Ghasemi, et al, Fabrication of Methane Sensor Using Inter-Digitated Electrode, Modified with Ag2O, SiO2, ZnO and MgO Nanoparticles-Mixed Multi-Walled Carbon Nanotubes as Specific Nanomaterials, Journal of Nanoengineering and Nanomanufacturing vol. 3, Sep. 3, 2013, pp. 202-210.

* cited by examiner

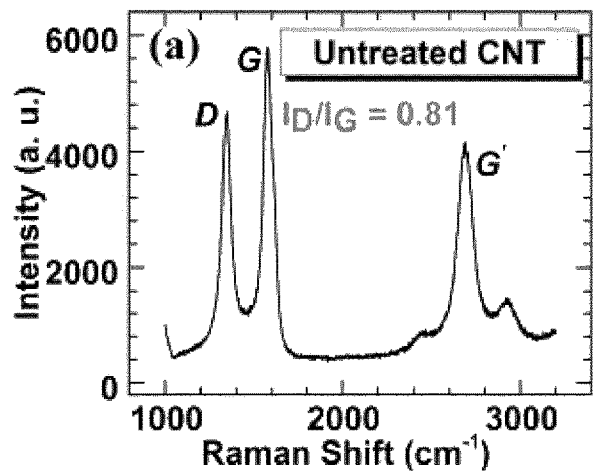
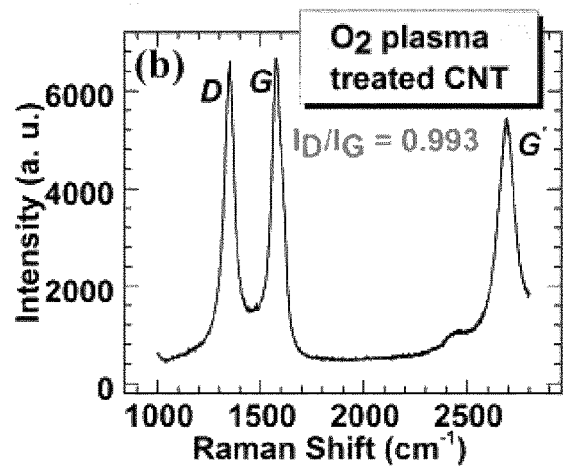
Figure 4A
Figure 4B
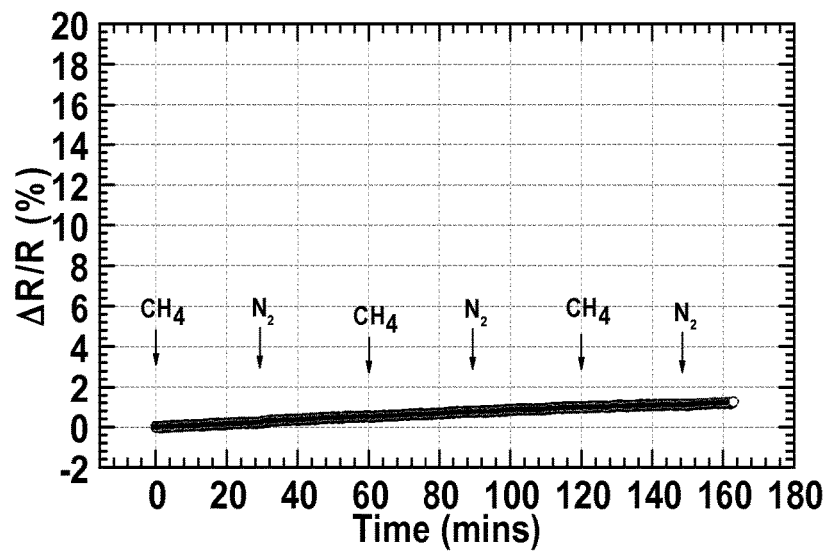
Figure 5A (a) 175 °C ALD (c) 220 °C ALD

PRE-TREATED FUNCTIONALIZED MULTI-WALLED CARBON NANOTUBE BASED METHANE SENSOR

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates to carbon nanotubes and sensors. More specifically, certain embodiments relate to pre-treated functionalized multi-walled carbon nanotube based methane sensor.

BACKGROUND OF THE INVENTION

Gas sensing technology has become more significant because of its widespread and common applications in the following areas: industrial production (e.g., methane detection in mines); automotive industry (e.g., detection of polluting gases from vehicles); (3) medical applications (e.g., electronic noses simulating the human olfactory system) (4) indoor air quality supervision (e.g., detection of carbon monoxide); (5) environmental studies Gas sensors are devices that transform partial pressures or gas compositions measured in air or gases into an electric signal. Gas sensors form a core part of gas sensing technologies and are increasingly needed in more flexible structures, with more sensitive detection limits, and utilizing more efficient materials.

While gas sensors can be made from a variety of materials, carbon nanotubes (CNTs) provide an attractive physical structure for sensors. However, CNTs are insensitive towards most target gases due to poor bonding between the chemically inert graphitic surface and different compounds to which they are exposed. Prior work has attempted to address this issue with surface pre-treatment. Importantly, the surface pre-treatment needed to achieve highly sensitive CNT chemiresistor based sensors must not disturb the morphology of the CNT. Previously reported CNT based methane ($CH_4$) sensors are characterized by a maximum relative resistance change of 2% and sensitivity 15 ppm $CH_4$. Those sensors use Pd as the functionalization which is not only very expensive but it also forms a significant Schottky barrier with bare CNT.

There remains a need for a CNT-based material that can be used in gas sensors.

SUMMARY OF THE INVENTION

One embodiment of the invention relates to a process for manufacturing a chemiresistor. The process includes fabricating electrodes on a substrate; depositing carbon nanotubes on the fabricated electrodes; pre-treating the carbon nanotubes to induce surface defects; and depositing a metal oxide functionalizing agent on the surface defects.

Another embodiment relates to a chemiresistor. The chemiresistor comprises a substrate having a plurality of electrodes. Carbon nanotubes are deposited on the electrodes, the carbon-nanotubes having a plurality of induced surface defects. The carbon nanotubes have a functionalizing agent comprising a metal oxide. The functionalizing agent is deposited on a portion of the plurality of induced surface defects.

Another embodiment relates to a method of sensing a gas. The method includes placing a chemiresistor in proximity to a gas and interacting the gas with a metal oxide functionalized pre-treated carbon nanotube, altering the resistance of the metal oxide functionalized pre-treated carbon nanotube.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1A The concept of low-cost $CH_4$ sensor, a die with 4 $CH_4$ sensors; FIG. 1B Au inter-digitated metal electrodes fabricated by photolithography; Figure C SEM image of MWCNT nanocomposite confined between two Au electrodes.

FIG. 2A SEM image of an $O_2$ plasma treated ZnO functionalized MWCNTs mesh. The bright layer covering the CNTs is ZnO, which was confirmed by the energy dispersive x-ray spectroscopy (EDS) FIG. 2B.

FIGS. 4A and 4B show: Raman spectra of FIG. 4A an untreated and FIG. 4B $O_2$ plasma treated MWCNT sample.

FIG. 5A shows relative resistance change of the ZnO functionalized MWCNT sensors while subjected to repetitive exposure of 10 ppm of $CH_4$ in dry air and $N_2$ (the MWCNT were not pre-treated).

FIG. 7A shows the Raman Spectroscopy for a sample fabricated using 175° C. FIG. 7B shows the Raman Spectroscopy for a sample fabricated using 200° C. FIG. 7C shows the Raman Spectroscopy for a sample fabricated using 220° C.

FIG. 9A shows a MWCNT sample where ALD was performed at 175° C. FIG. 9B illustrates the size distribution of ZnO nanoparticles for the sample of FIG. 9A. FIG. 9C shows a MWCNT sample where ALD was performed at 200° C. FIG. 9D illustrates the size distribution of ZnO nanoparticles for the sample of FIG. 9C.

DETAILED DESCRIPTION OF THE PREFERRED EMBODIMENTS

Figure 1A:
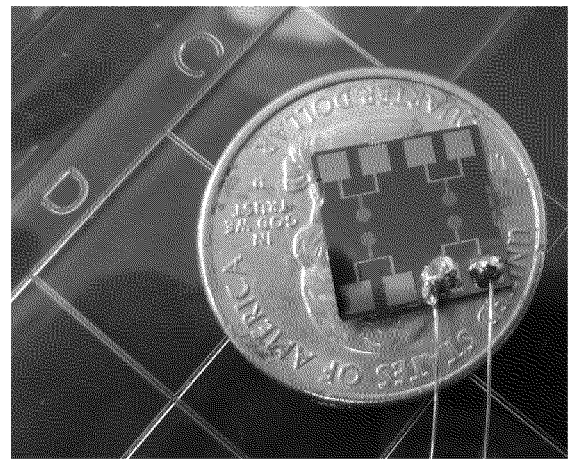
FIGS. 1A-1C.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Described herein are processes, articles of manufacture and systems relating to pre-treatment and functionalization that enables methane. One aspect relates to surface activation of CNTs using UV Ozone and oxygen plasma, to induce surface defects, combined with ZnO atomic layer deposition (ALD) functionalization to produce a highly sensitive methane sensor. Another aspect relates to selective functionalization of CNT mesh using microfabricated stenciled masks and E-beam evaporation of functionalization material to increase selectivity in presence of interfering gasses by destructive/constructive interference within a chemresistive circuit. A third aspect relates to MEMS-based atomic layer deposition (ALD) system and its use to selectively functionalize CNT mesh to enhance selectivity to methane in presence of interfering gasses.

Methane sensors according to one embodiment provide for detection at near background methane levels (~1.8 ppm), including at 1 ppm, 2 ppm, 3 ppm, less than 15 ppm, less than 10 ppm, less than 4 ppm at room temperature with average Relative Resistance Change (RRC) of more than 10%.

Surface Pre-Treatment and Functionalization

Metal-oxides are commonly used as a material for methane sensors. Metal oxide based sensors present several disadvantages. For example, continuous heating is necessary to initiate the surface chemisorption of oxygen, often requiring 100s of mWs of power. In contrast, it has been shown that CNT-based methane sensors can detect ppm levels of $CH_4$ at room temperature, with power consumption of only few mWs.

Previously reported CNT-based $CH_4$ sensors with maximum relative resistance change of 1% (at 6 ppm $CH_4$) use Pd as the functionalizing material. However, the reliance on Pd results in a significant Schottky barrier with bare CNT. In addition, the underlying CNT presents a chemically inert graphitic surface that exhibits a relatively poor bond with the functionalization compound. Consequently, surface pre-treatment of CNTs is necessary to achieve highly sensitive CNT chemiresistor-based sensors. Further complicating the creation of CNT-based sensors, this necessary surface pre-treatment must be such as not to disturb the morphology of the CNTs.

In one embodiment, ZnO is used as a functionalizing material for MWCNT. ZnO, which is less expensive than Pd, also provides an energetically favorable electron transport in ZnO-MWCNT junction.

Figure 1B:
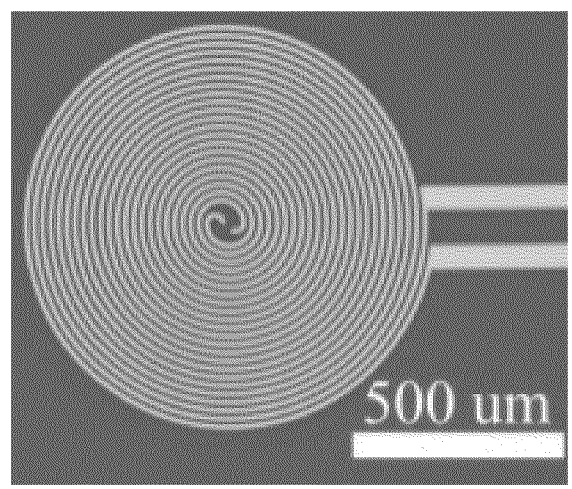
Figure 1C:
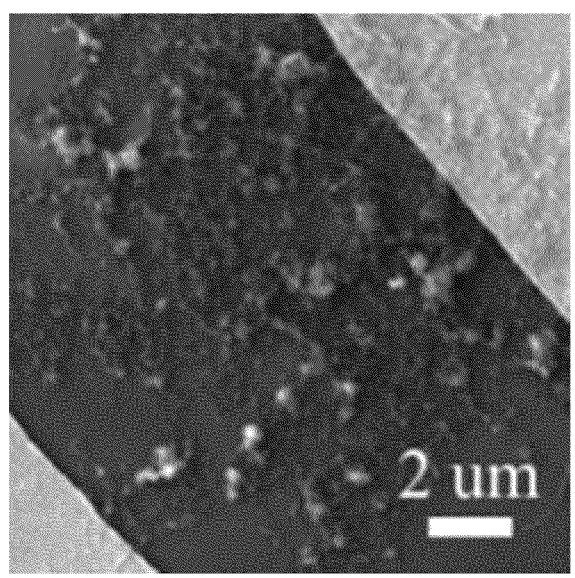

FIGS. 1A-1C illustrate one embodiment for a $CH_4$ chemiresistor for natural gas applications (methane detection). In FIG. 1A shows a die with four chemiresistive methane sensors. The Au electrodes were fabricated using a lift-off based photolithography technique. FIGS. 1B and 1C show magnified views of the structure.

In one embodiment, CNTs are deposited on the fabricated electrodes. The CNT may be multi-wall carbon nanotubes ("MWCNT"), which provide for additional surface area over single-walled carbon nanotubes ("SWCNT"). MWCNTs are preferred over SWCNT, although SWCNT may be used. MWCNT generally provide additional advantages, such as, lower expense, easier growth process and more surface area (not "specific surface area"). For embodiments illustrated in the accompanying figures, a solution, such as an alcohol, e.g., ethanol, and MWCNTs was drop deposited on the fabricated electrodes. An ultrasonicated solution of 1 mg/50 mL of MWCNTs in ethanol was used to produce a well dispersed MWCNT mesh. Using a microsyringe, 50 μL aliquot was deposited on an 1 $mm^2$ active area of the fabricated metal electrodes, which was followed by baking at 75° C. to remove the solvent and to improve adhesion. The drop deposition may be by 2-3 drops on the sample. The solvent is evaporated such as at 75° C. on a hot plate. A set of interdigitated gold (Cr/Au) electrodes were fabricated on the $SiO_2$ coated Si wafer, implementing a lift-off based photolithography technique. A bi-layer of Microchem Lift-Off Resist 3A (LOR 3A) and S 1813 photoresists was spin-coated onto the $SiO_2$/Si wafer while a direct laser writer (LW 405) was used to do the optical exposure. After the development process a 100 nm Au film on top of a 10 nm Cr layer was deposited on the patterned photoresist using a PVD 250 Lesker e-beam evaporator. Deposited metal was lifted off by ultrasonicating the samples immersed in an 1165 remover bath (FIG. 4F). The gap between the interdigitated electrodes was 10 μm.

Then, the deposited CNT were pre-treated. In one embodiment, the pre-treatment was by $O_2$ plasma in a reactive ion etching chamber for 5 min. The pre-treatment may be done for 1-20 minutes, including for 3 minutes, 4 minutes, 5 minutes, 6 minutes, 7 minutes, 8 minutes, 9 minutes, 10 minutes, 11 minutes, 12 minutes, 13 minutes, 14 minutes. Although oxygen plasma is described in the examples herein, alternative embodiments utilize other types of plasma, such as argon plasma.

In another embodiment, pre-treatment of the CNT was by UV and $O_3$ exposure. The pre-treatment by exposure to $O_3$ and UV may be done for 1-20 minutes, including for 3 minutes, 4 minutes, 5 minutes, 6 minutes, 7 minutes, 8 minutes, 9 minutes, 10 minutes, 11 minutes, 12 minutes, 13 minutes, 14 minutes. In one particular embodiment, the pre-treatment is for 20 minutes.

Next, the pre-treated CNTs are functionalized. In one embodiment, there is no purge step prior to the ALD proceeding. In one embodiment, ZnO is utilized as the functionalizing agent. Other metal oxides, including but not limited to $SnO_2$, $InO_3$, $Al_2O_3$, $TiO_2$, may be deposited using appropriate precursors. The chemiresistor may consist essentially of one metal oxide, such as ZnO. ZnO was deposited on the pre-treated CNTs using ALD. The deposition temperature may be between 175° C. and 225° C., such as at 175° C., 200° C., or 220° C. In one embodiment, ZnO was deposited on the plasma treated CNTs by an Arradiance Gemstar ALD tool at 175° C. with diethylzinc as the precursor and with water as the oxidizer. In one embodiment dimethyzinc may be used as the precursor for ZnO. In one embodiment, the ALD process proceeds until 2 nm of ZnO has been deposited, alternatively 1 nm, 1.25 nm, 1.5 nm, 1.75 nm, 2 nm, 2.25 nm, 2.5 nm, 2.75 nm, 3 nm, 3.25 nm, 3.5 nm, 3.75 nm, or 4 nm. In another embodiment, the ALD process proceeds for 8 cycles. Alternatively, 4-16 cycles or any number therein.

Figure 10:
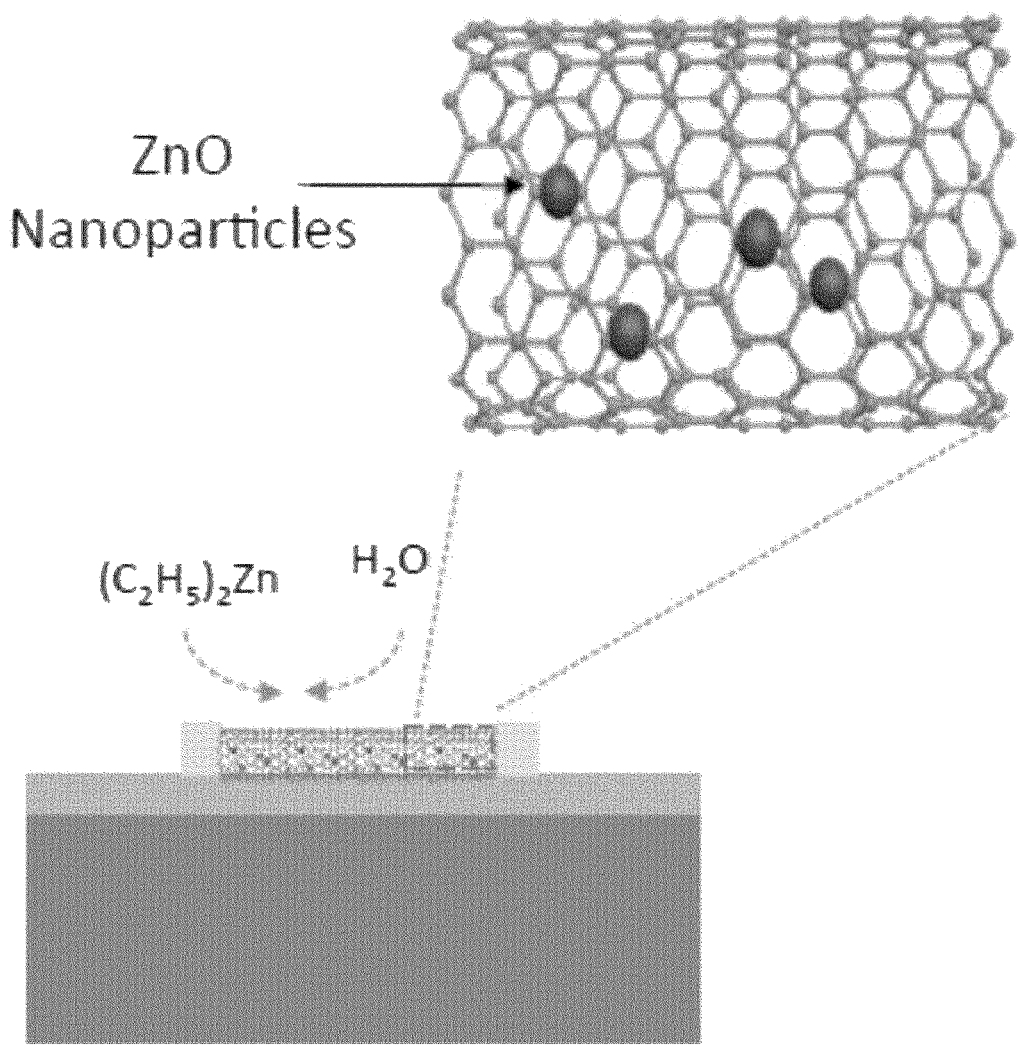
FIG. 10 depicts ALD deposition of ZnO on CNT.

FIG. 10 depicts one mechanism of ALD deposition of ZnO on CNT. ALD deposition of the functionalizing agent allows for precise sub-nanometer control and thickness. ALD deposition also preserves high homogeneity and conformality as well as providing a deposition technique that is independent of the complexity of the substrate.

The functionalized CNT may be "recovered" by an exposure to nitrogen or dry air.

Figure 2A:
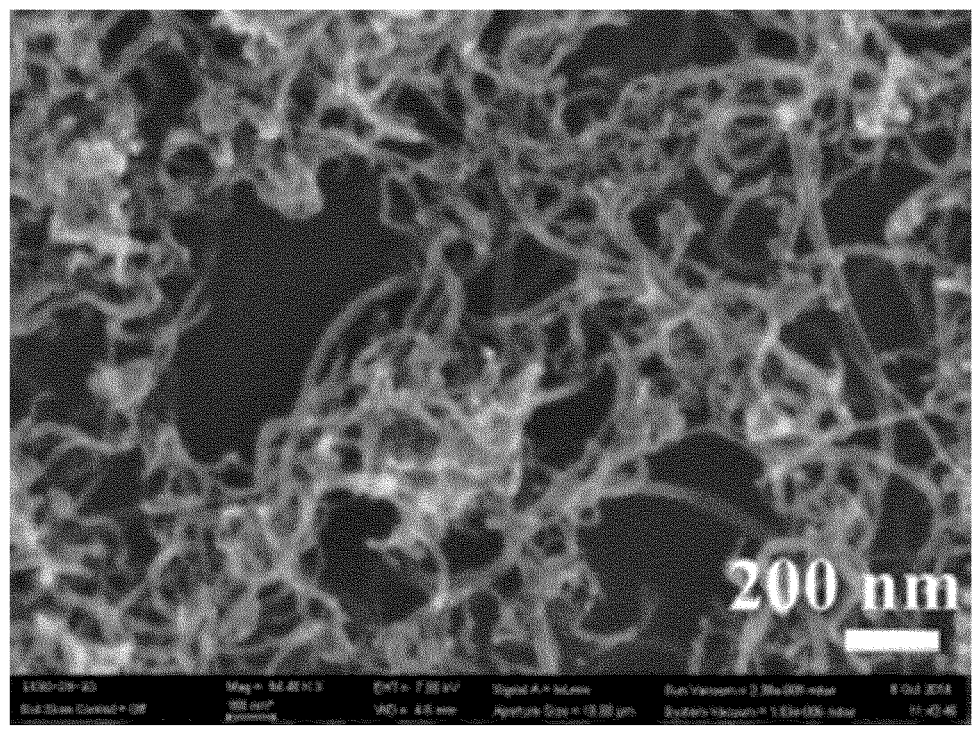
FIGS. 2A-2B show.
Figure 2B:
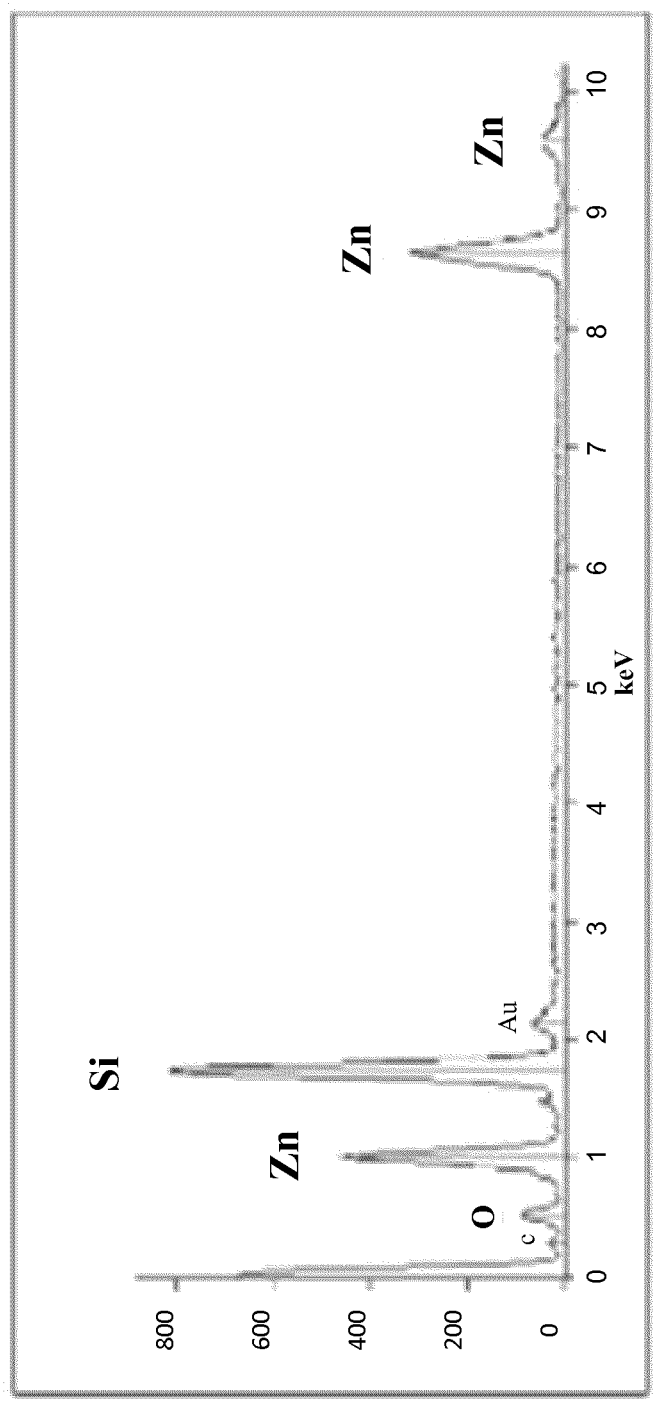
Figure 3A:
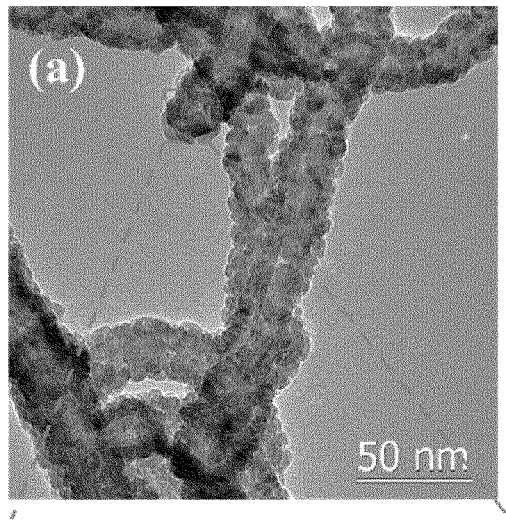
FIG. 3A shows transmission electron microscopy (TEM) image of uniform distribution of atomic layer deposited ZnO nanoparticle (NP) layers on the UV-$O_3$ pre-treated MWCNT surface.
Figure 3B:
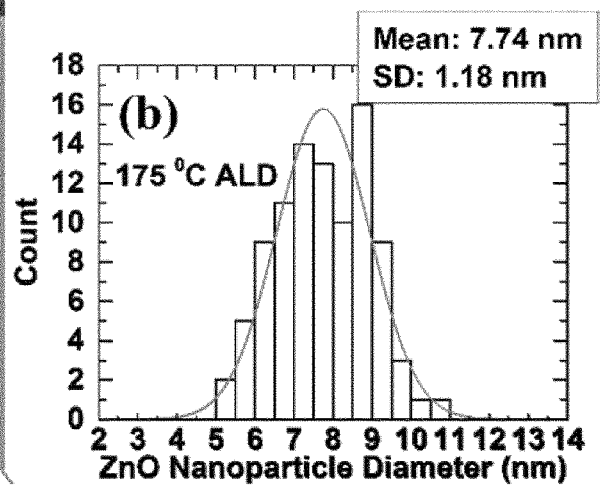
FIG. 3B shows a higher resolution TEM image in illustrating the wurtzite structure of the ZnO NP and its good crystalline quality. The interplanar spacing of 2.8 Å, 2.68 Å and 2.48 Å correspond to <100>, <002> and <101> planes of ZnO. ZnO nanoparticles are not visible on the surface of the untreated MWCNTs as can be seen in FIG. 3B.
Figure 3C:
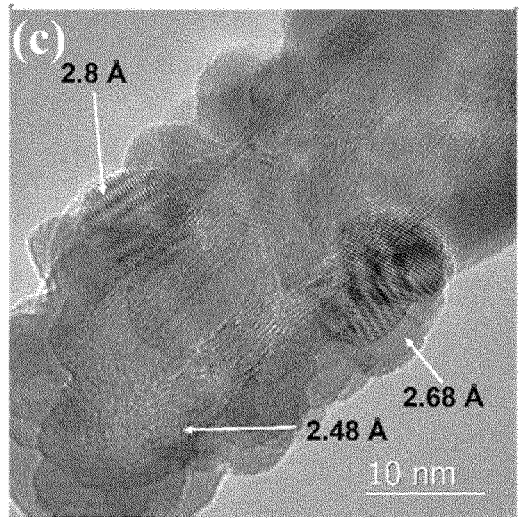
FIG. 3C shows size distribution, with mean diameter of the ZnO nanoparticles is 7.74 nm.
Figure 3D:
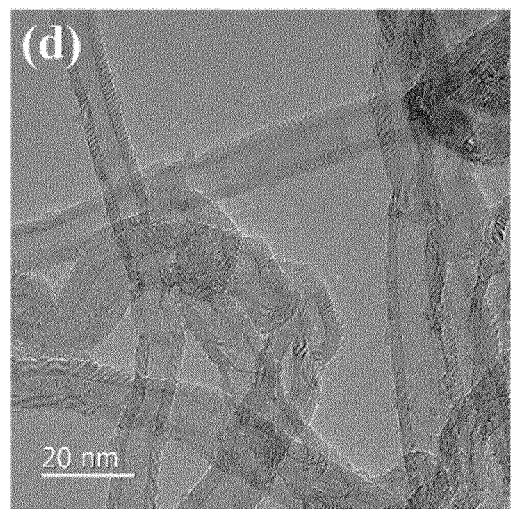
FIG. 3D shows a sample that was not-pretreated but was functionalized.
Figure 8:
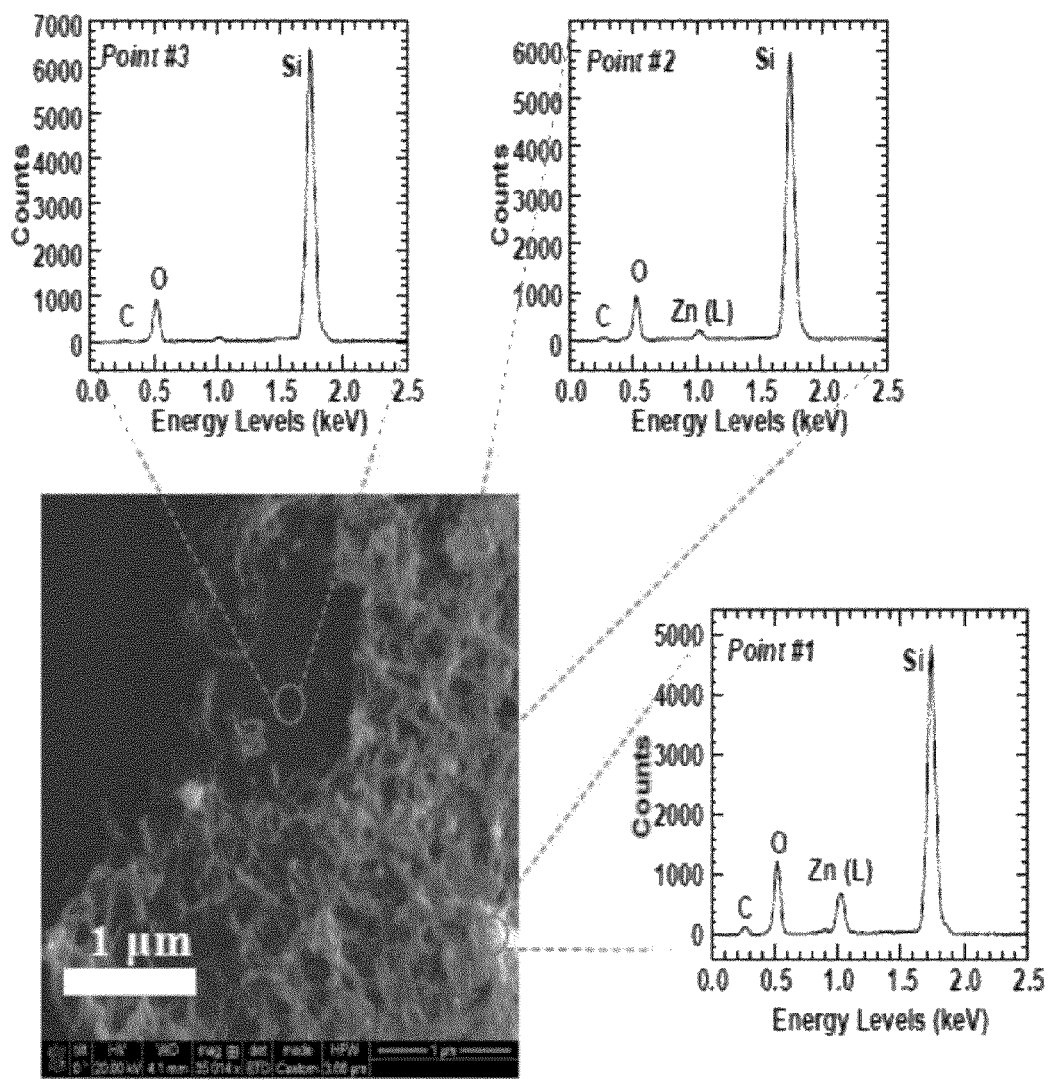
FIG. 8 shows energy dispersive x-ray spectroscopy (EDS) results.

The morphology of the functionalized MWCNTs was characterized by scanning electron microscope (SEM) and the chemical composition was confirmed by energy dispersive x-ray spectroscopy (EDS) (FIGS. 2B and 8) and transmission electron microscopy (TEM) (FIG. 3). FIG. 2B depicts the FIG. 8 shows energy dispersive x-ray spectroscopy (EDS) results.

Figure 9A:
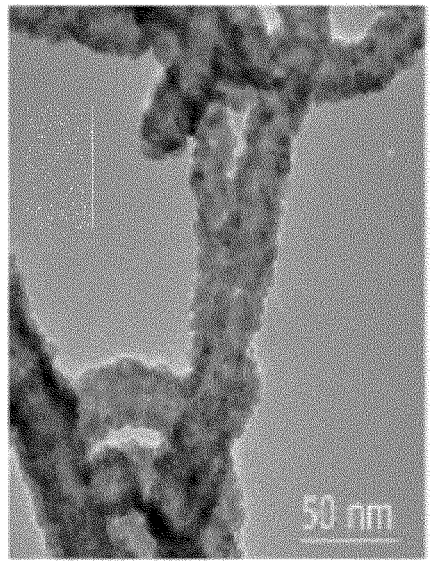
FIGS. 9A-D illustrate TEM images and particle size distribution.
Figure 9B:
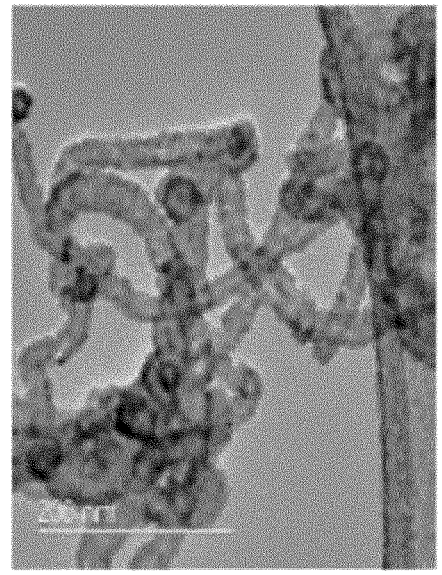
Figure 9C:
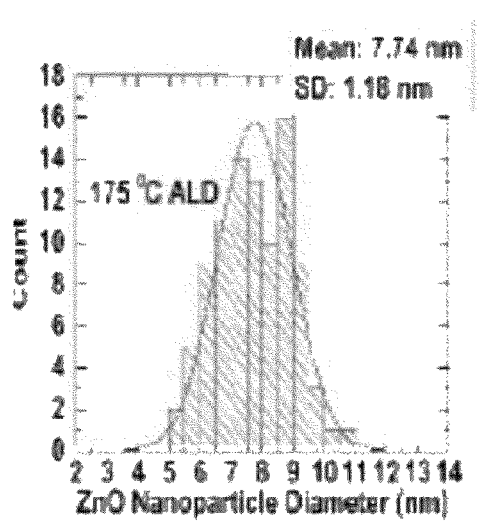
Figure 9D:
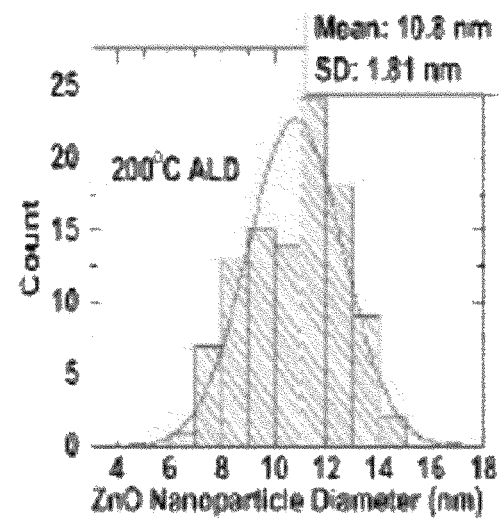

FIGS. 9A-D illustrate TEM images and particle size distribution. FIG. 9A shows a MWCNT sample where ALD was performed at 175° C. FIG. 9B illustrates the size distribution of ZnO nanoparticles for the sample of FIG. 9A. FIG. 9C shows a MWCNT sample where ALD was performed at 200° C. FIG. 9D illustrates the size distribution of ZnO nanoparticles for the sample of FIG. 9C.

Figure 7A:
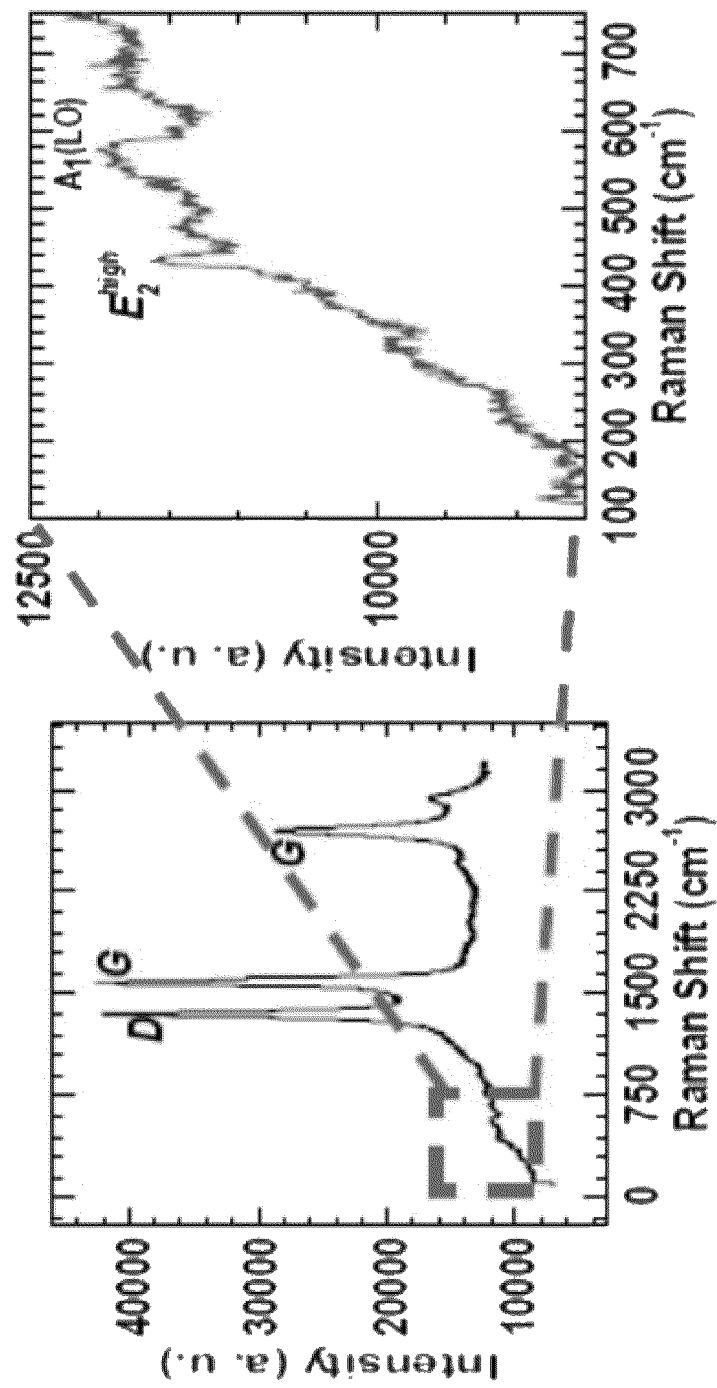
FIGS. 7A-C illustrate Raman spectroscopy of ZnO MWCNT illustrating characteristic peaks originating from both ZnO and MWCNTs.
Figure 7B:
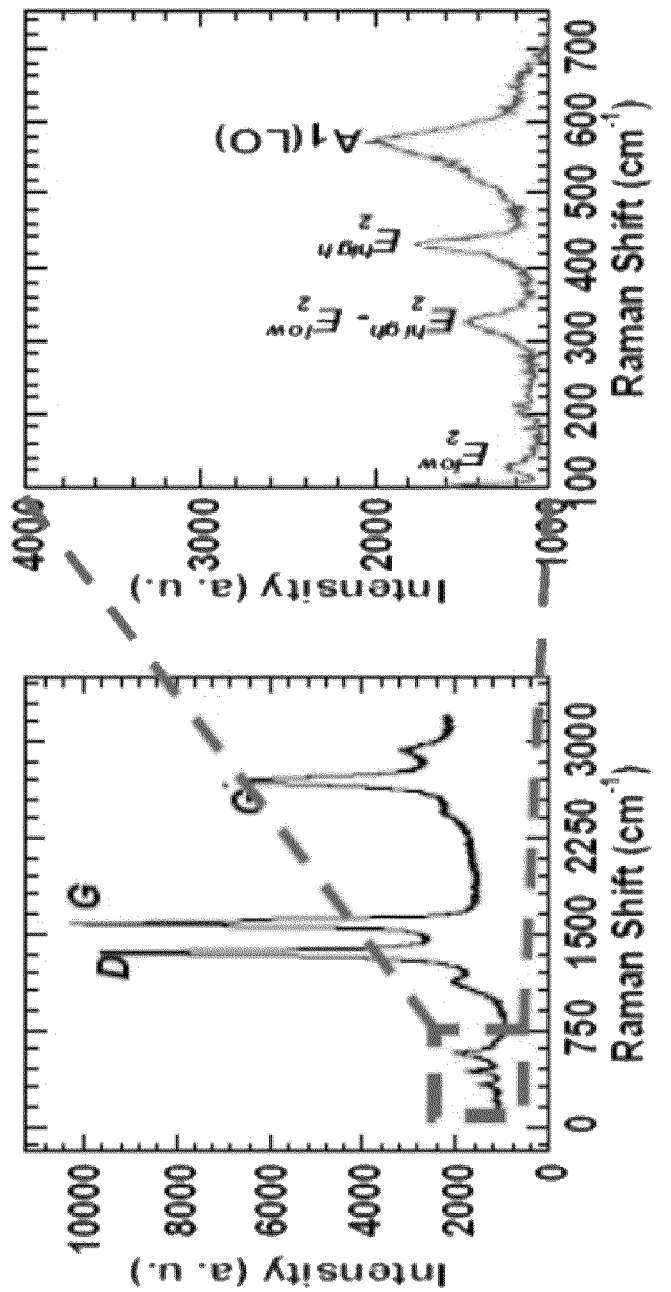
Figure 7C:
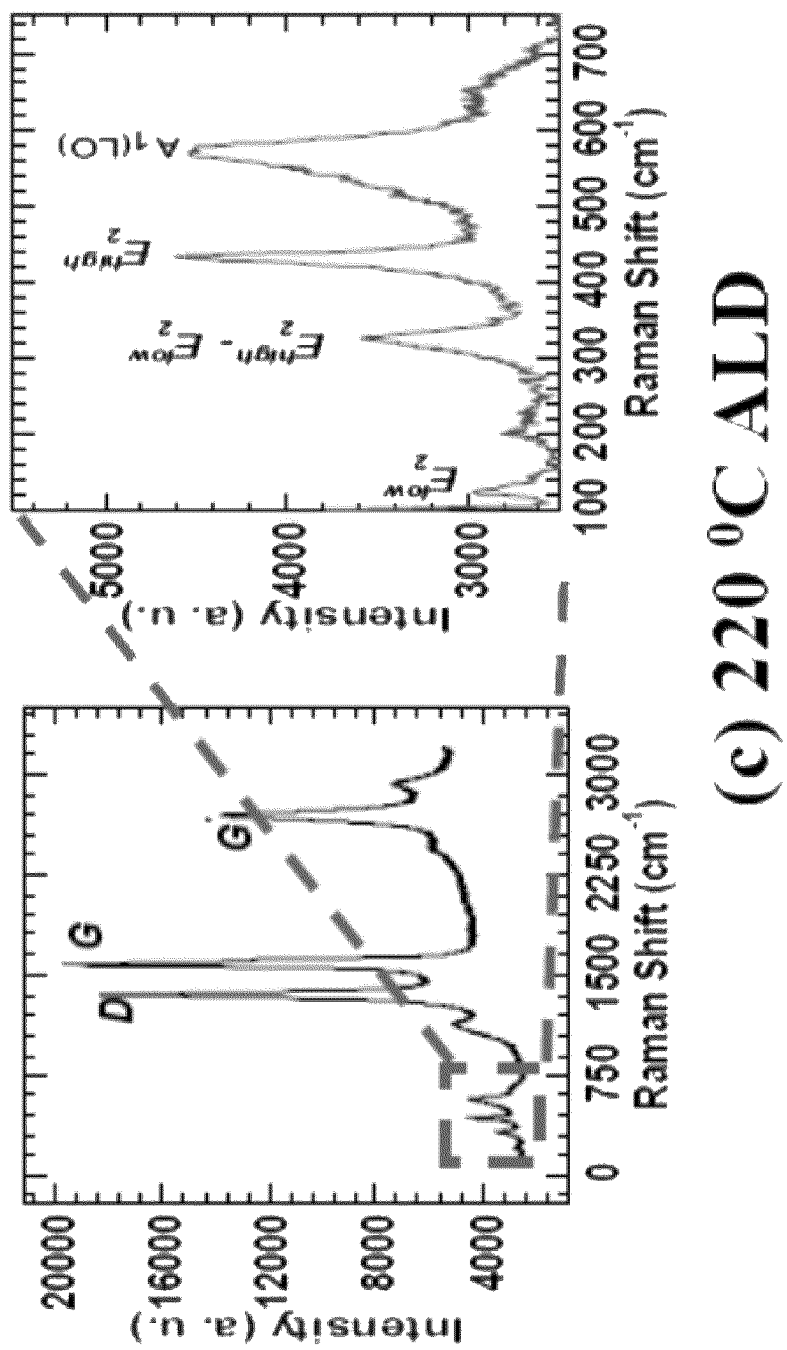
Figure 7D:
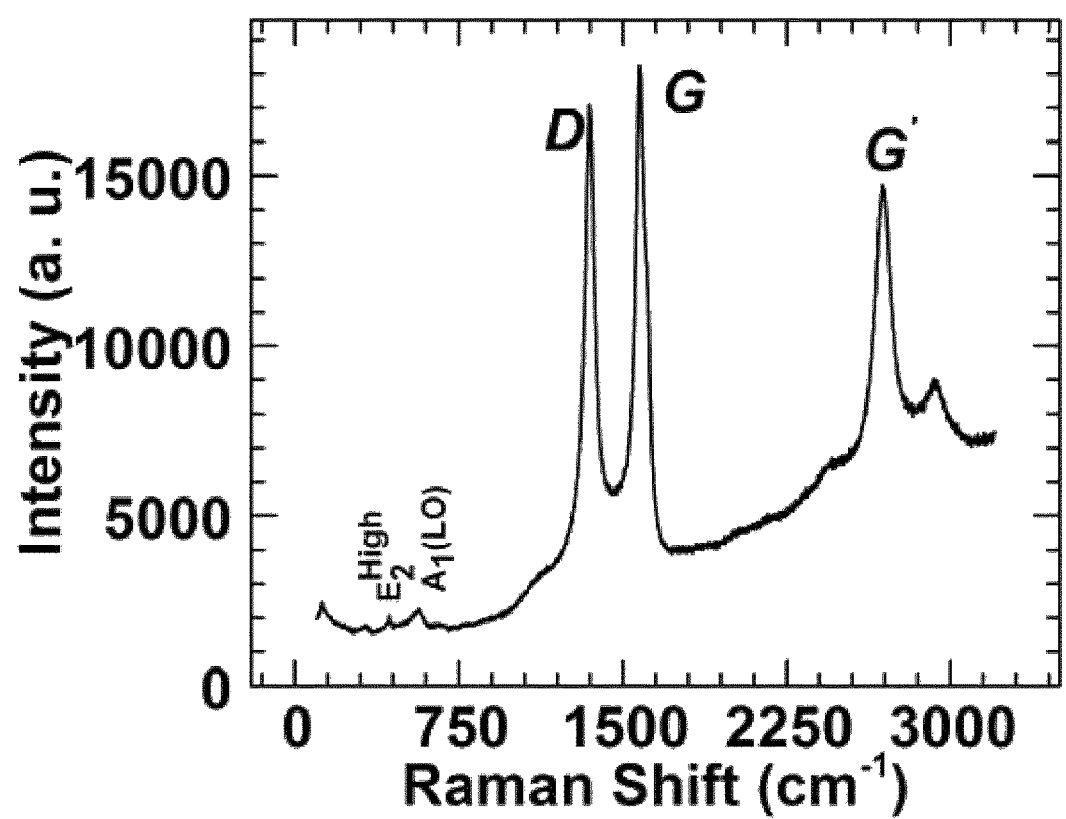
FIG. 7D shows Raman Spectroscopy for UV-$O_3$ treated ZnO functionalized sample.

The graphitic quality of the pristine and plasma treated MWCNT were characterized by the Raman spectroscopy using a green laser. Raman spectra were acquired at various location of the sensor and the average of the relative intensity of the D-peak with respect to the G-peak ($R=I_D/I_G$) was calculated (FIG. 4). R increases 13.5% for $O_2$ plasma treated MWCNT with respect to the un-treated ones, which indicate the presence of reactive defect sites on the surface. FIGS. 7A-C illustrate Raman spectroscopy of ZnO-MWCNT illustrating characteristic peaks originating from both ZnO and MWCNTs. FIG. 7D shows characteristic Raman peaks of ZnO and CNT appeared from a UVO pre-treated ZnO functionalized MWCNT sample. FIG. 7A shows the Raman Spectroscopy for a sample fabricated using 175° C. FIG. 7B shows the Raman Spectroscopy for a sample fabricated using 200° C. FIG. 7C shows the Raman Spectroscopy for a sample fabricated using 220° C. The Raman Spectroscopy results establish that ZnO-MWCNT have characteristic peaks originating from both ZnO and MWCNTs. The Raman peaks strength and sharpness is ALD temperature dependent. Superior crystal quality is observed at higher temperature ALD.

Figure 5B:
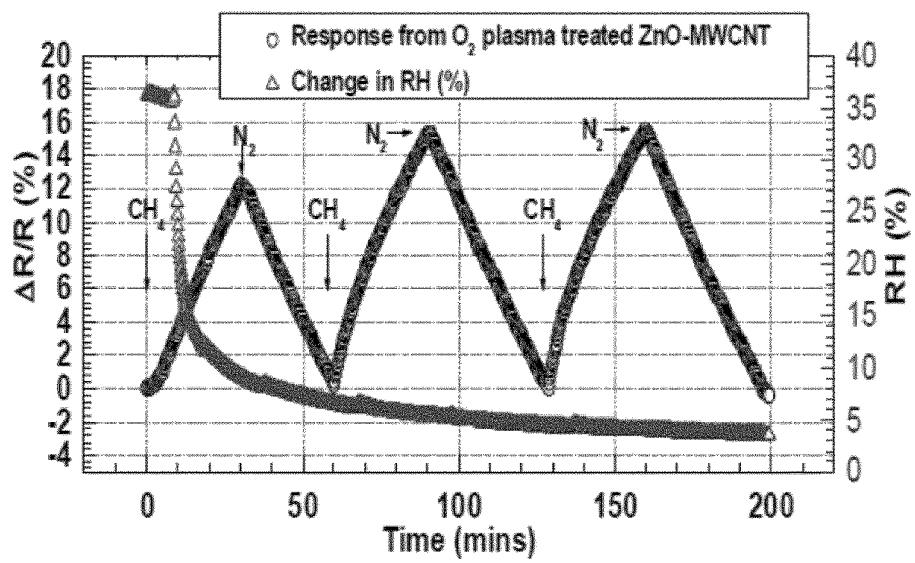
FIG. 5B illustrates relative resistance change of the pristine MWCNT while subjected to repetitive exposure of 10 ppm of $CH_4$ in dry air and $N_2$ responsiveness for an $O_2$ plasma treated MWCNT prior ZnO functionalization.
Figure 5C:
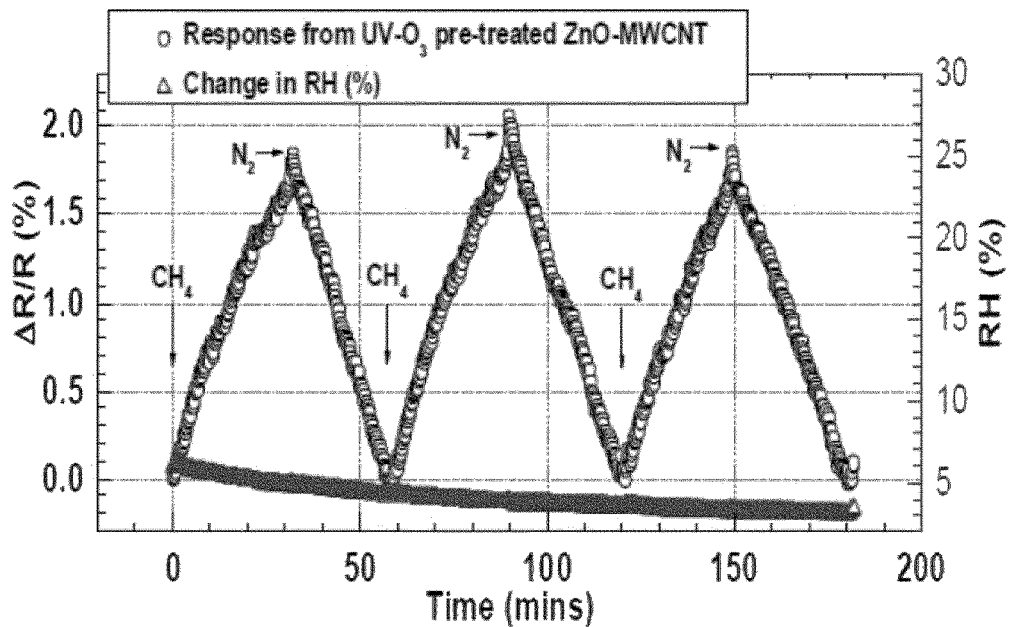
FIG. 5C illustrates relative resistance change of the pristine MWCNT while subjected to repetitive exposure of 10 ppm of $CH_4$ in dry air and $N_2$ responsiveness for a UV-$O_3$ pre-treated MWCNT prior ZnO functionalization. The RRC is much less for UVO sample compared to $O_2$ plasma. Hence, $O_2$ plasma pre-treated and ZnO functionalized MWCNT methane sensor showed superior performance compared to UVO pre-treated ZnO functionalized MWCNT methane sensor.

Raman results showed that as the ZnO ALD temperature increases the crystal quality of the ZnO NCs on the MWCNT surface is enhanced. Superior crystal quality of the functionalizing ZnO NCs enhances the electron transport in the ZnO-MWCNT junction thus has positive impact on the sensor performance with respect to relative resistance change, i.e., sensitivity. It is important to ensure the chemical stability and robustness of the functionalizing material so that the sensor operates accurately in harsher environments. High crystal quality of the functionalizing NCs helps minimize cross-response and optimize reversibility as the sensor ages. A stencil mask based fabrication technique will allow utilizing MWCNT functionalized with ZnO deposited at a higher temperature Surface pre-treated ZnO-MWCNT sensors show stronger response to ppm level of $CH_4$ comparing to untreated ZnO-MWCNT sensors. FIG. 5A shows the relative resistance change of the ZnO functionalized MWCNT sensors while subjected to repetitive exposure of 10 ppm of $CH_4$ in dry air and $N_2$. FIG. 5B shows relative resistance change of the pristine MWCNT while subjected to repetitive exposure of 10 ppm of $CH_4$ in dry air and $N_2$. The increase in relative resistance change is notable from The relative resistance of the sensors was measured at various ppm concentration of $CH_4$ inside a test chamber where an air mixture of calibration $CH_4$ was introduced and the ppm was continuously monitored by a reference $CH_4$ detector. FIG. 10A illustrates responsiveness for an $O_2$ plasma treated ZnO MWCNT. FIG. 10B illustrates responsiveness for a UV-O3 pre-treated ZnO MWCNT.

The observed change in sensitivity comparing to the previously reported functionalized CNT chemiresistors is in part a result of implementing ZnO atomic layer deposition (ALD) functionalization with $O_2$ plasma and UV-$O_3$ pre-treatment of the CNTs to induce surface defects, enhancing ZnO affinity. Use of ZnO in lieu of Pd for CNT functionalization, coupled with drop-deposition of CNTs significantly reduces the complexity and cost of the fabrication process.

Selective Functionalization Using Shadow Mask and E-Beam Evaporation

In one embodiment, the CNT are functionalized using a masking technique to selectively functionalize the CNTs to a gas by "more gas-specific" and "less gas-specific" nanoparticles. The gas may be, for example, methane. The use of a masking technique will allow controllable exposure of segments of CNT, avoiding the chance of contamination or destruction by chemicals and heat treatments associated with conventional lithographic processes.

The nanoscale shadow mask will be placed on the CNT devices to selectively deposit ZnO nanoparticles on some part of it and $SnO_2$ nanoparticles on other portions. In one embodiment, ZnO and $SnO_2$ nanoparticles will be deposited on the masked CNT meshes by thin film sputtering. The shadow mask will facilitate the fabrication of a differential grid of CNTs selectively functionalized with ZnO and $SnO_2$. The grid will be able to selectively detect $CH_4$ in presence of interference gases. The chemiresistor sensor can be expanded into a differential grid consisting of selectively functionalized CNT that will be able to selectively detect a target gas, such as $CH_4$, in presence of interference gases, such as $H_2O$, $CO_2$, $O_2$, $H_2$, CO. Differential grid-based chemiresistor sensors can also be employed to determine and nullify the interference caused by variable relative humidity during CH$_4$ sensing. Differential grid-based chemiresistor sensors can also be employed to determine and nullify interference caused by variable relative humidity during CH$_4$ sensing.

MEMS Based Micro-ALD

Further, in one embodiment a small scale a small-scale microfabricated atomic layer deposition (ALD) chamber is utilized. The small-scale chamber can be placed over a small region of the substrate and be used to selectively deposit thin films and grow nanoscale hetero-structures using the ALD process.

Figure 6:
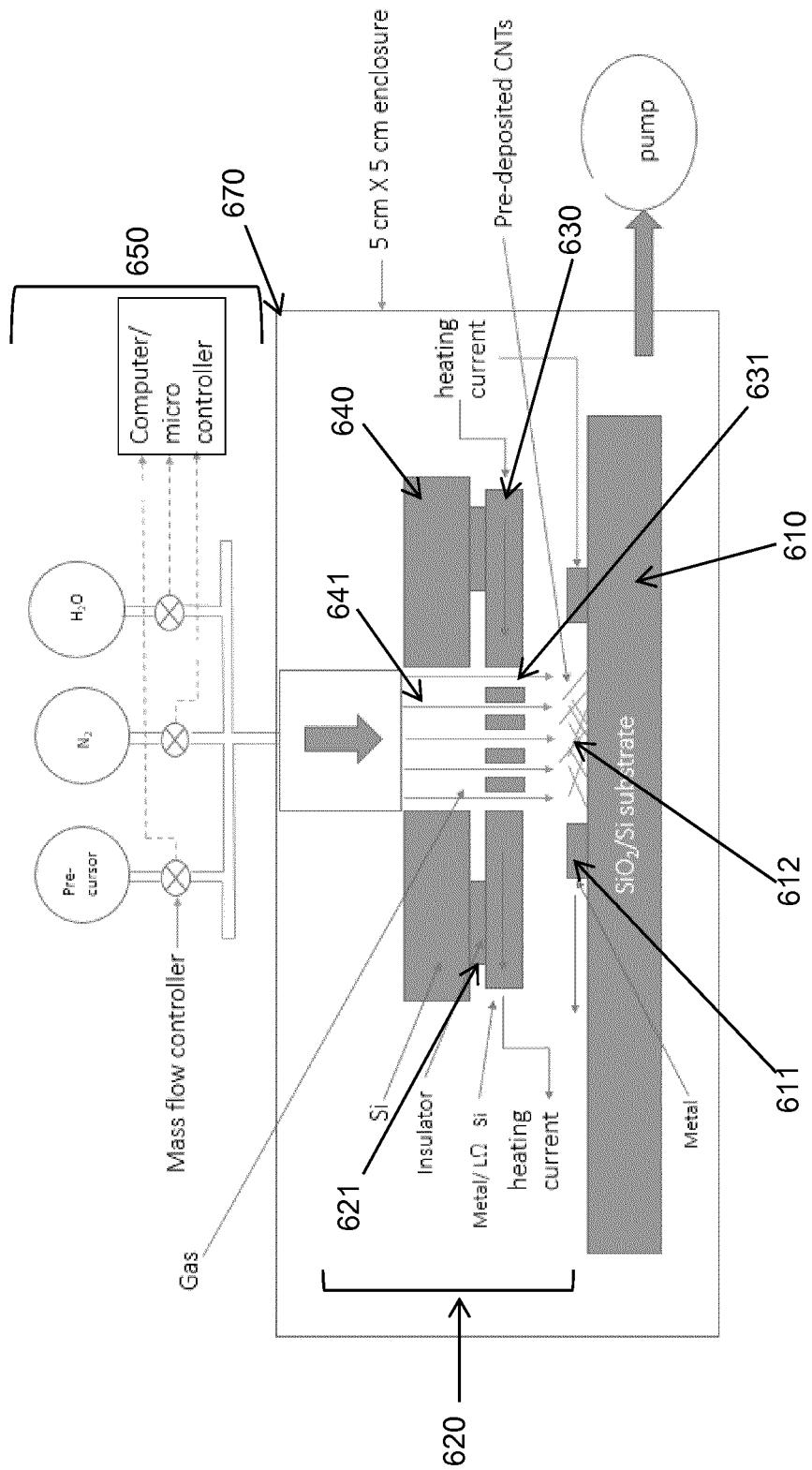
FIG. 6 illustrates one embodiment of a small-scale microfabricated atomic layer deposition (ALD) chamber that can be placed over a small region of the substrate and be used to selectively deposit thin films and grow nanoscale heterostructures using the ALD process.

FIG. 6 illustrates one embodiment of an apparatus for microfabrication using ALD. A substrate 610 is provided. The substrate includes electrodes 611 and CNT 612. An ALD device 620 is positioned. The ALD device includes a heating element 630 and a body 640. The heating element 630 may be heated by application of a heating current. An insulator 621 may be provided to separate the heating element 630 from a body 640. The body 640 receives the ALD gases 650, including precursors, oxidizers, and purge gases, as well as any liquid or vapor components. The gases are directed through a passage 641 in the body 640 and through at least one passage 631 in the heating element 630. In one embodiment, the heating element 630 includes multiple passages 631 allowing for thermal energy transfer from the heating element 630 to the gases. The at least one passage in the heating element 630 is aligned over the substrate 610, such as over all or a portion of the CNTs to deposit a material via ALD. In one embodiment, the entire substrate 610 and ALD device 620 is contained within an ALD chamber 670, such as a 5 cm by 5 cm chamber 670. The source of gases 650 may be external to the chamber 670. The microfabricated ALD apparatus allows for selective positioning and thus selective functionalization of materials, such as CNTs.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A process for manufacturing a chemresistor comprising:
    fabricating electrodes on a substrate;
    depositing carbon nanotubes on the fabricated electrodes;
    pre-treating the carbon nanotubes for 1-20 minutes with ozone and UV to induce surface defects; and
    depositing by atomic layer deposition, a plurality of nanoparticles consisting of a metal oxide functionalizing agent on the surface defects.

2. The process of claim 1, wherein depositing the carbon nanotubes comprises dissolving the carbon nanotubes in a solvent, depositing the solution on the fabricated electrodes, and removing the solvent.

3. The process of claim 1, wherein atomic layer deposition is at a temperature between 175° C. and 220° C.

4. The process of claim 3, wherein the temperature is 200° C. to 220° C.

5. The process of claim 4, wherein the atomic layer deposition includes the step of exposing the carbon nanotubes to a first precursor comprising diethylzinc and a second precursor comprising water.

6. The process of claim 1, wherein the deposited carbon nanotubes are multi-walled carbon nanotubes (MWCNT).

7. The process of claim 6, wherein depositing the MWCNT further comprises drop depositing a solution of MWCNT and baking until the solvent is evaporated.

8. The process of claim 1, further comprising selective functionalization.

9. The process for manufacturing a chemresistor of claim 1, wherein the deposited metal is deposited to a thickness of 1-4 nm.

* * * * *